United States Patent [19]

Kogure et al.

[11] Patent Number: 4,855,229

[45] Date of Patent: Aug. 8, 1989

[54] MEASUREMENT METHOD OF PEROXIDASE ACTIVITY

[75] Inventors: Eriko Kogure, Sagamihara; Makoto Nakamura; Toshiaki Kumazawa, both of Hachioji, all of Japan

[73] Assignee: Olympus Optical Co., Ltd., Tokyo, Japan

[21] Appl. No.: 936,320

[22] Filed: Dec. 1, 1986

[30] Foreign Application Priority Data

Dec. 5, 1985 [JP] Japan ............................. 60-272426

[51] Int. Cl.$^4$ ........................... C12Q 1/28; C12N 9/96
[52] U.S. Cl. ...................................... 435/28; 435/188; 435/810
[58] Field of Search ................... 435/28, 188, 810; 436/66

[56] References Cited

U.S. PATENT DOCUMENTS 4,193,938  3/1980  White .................................. 564/437
4,728,608  3/1988  Roberts et al. ........................ 435/34

OTHER PUBLICATIONS

Porstmann et al., J. Clin. Chem. Clin. Biochem., vol. 23 (1985), pp. 41–44.

Primary Examiner—Esther M. Kepplinger
Attorney, Agent, or Firm—Frishauf, Holtz, Goodman & Woodward

[57] ABSTRACT

A measurement method of peroxidase activity is based on reaction of o-phenylenediamine and hydrogen peroxide in the presence of peroxidase. This method includes preparing and storing a first reagent containing o-phenylenediamine and having a first pH value higher than a second pH value at which the reaction is conducted, and preparing and storing a second reagent having a buffering capability larger than the first reagent. At the time of measurement, the stored first and second reagents are mixed together with a sample containing peroxidase, and a predetermined amount of hydrogen peroxide to provide a reaction mixture having the second pH value. The reaction is conducted in the reaction mixture, thereby producing 2,2'-diamino-azobenzene, and the absorbance increase at the maximum absorption wavelength of the produced 2,2'-diaminoazobenzene is measured.

15 Claims, 1 Drawing Sheet

F I G. 1
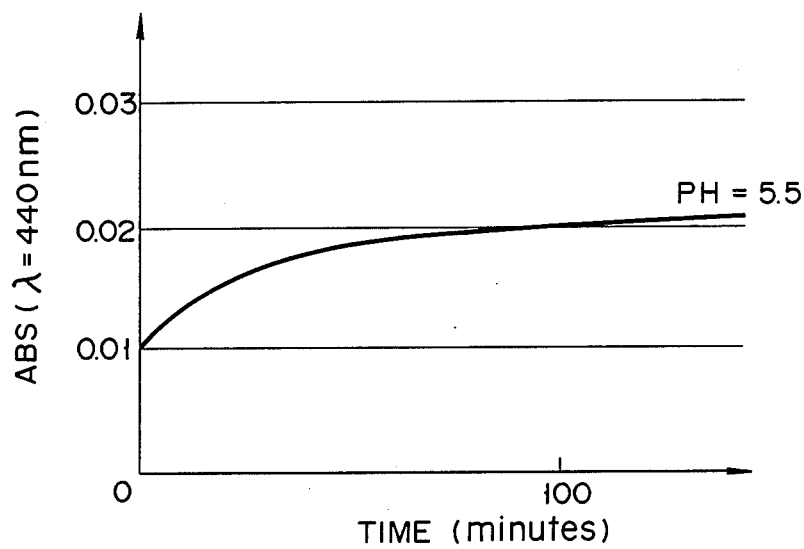
F I G. 2
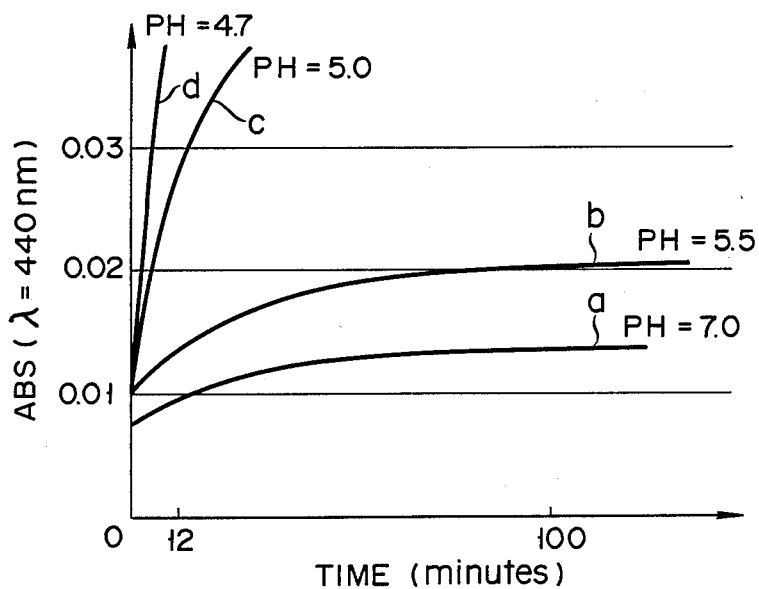

MEASUREMENT METHOD OF PEROXIDASE ACTIVITY

BACKGROUND OF THE INVENTION

1. Field of Invention

This invention relates to the method of measuring peroxidase activity.

2. Description of the Prior Art

"Peroxidase" (POD) is a general term for enzyme which catalyzes the oxidizing reaction as expressed in the following general equation. This enzyme is widely distributed in animal and vegetable tissues.

$$AH_2 + H_2O_2 (\text{or } CH_3OOH) \rightarrow A + 2H_2O (\text{or } 2CH_2OH)$$

Conventionally, to measure POD activity, o-phenylenediamine (OPD) is reacted with hydrogen peroxide ($H_2O_2$), by using POD sample. This is a color reaction which produces 2,2'-diamino-azobenzene as shown in the next equation. Consequently, from the absorbance increase at maximum absorption wavelength ($\lambda$ max.) of the 2,2'-diamino-azobenzene, the POD catalytic intensity, that is, the POD activity can be measured.

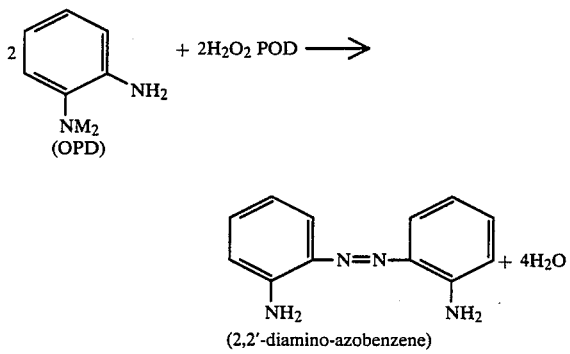

To perform the above method, the reagent containing OPD and $H_2O_2$ is used in the above enzyme reaction. This reagent is treated with a buffer liquid to have its pH value adjusted to 4.0 to 6.0, which is optimal for the enzyme reaction.

The above-mentioned reagent is prepared beforehand and kept in cold-storage in a dark place, and is then added to the sample containing POD at the actual measurement.

However, OPD and $H_2O_2$ will react slightly without POD, to give out 2,2'-diamino-azobenzene. Furthermore, this non-enzyme reaction also can somewhat easily take place at the optimum pH level for the enzyme reaction by the POD. For this reason, the conventional reagent adjusted to POD optimum pH level will gradually react during storage. Thus, when this reagent is used, the foregoing absorbance of the reagent increases to a certain extent. For example, in the case of the conventional reagent adjusted to a pH value of 5.5 and stored at 4° C., its absorbance at maximum absorbance wavelength ($\lambda$ max.=440 nm) of the 2,2'-diamino-azobenzene doubles in about 100 minutes as shown in FIG. 2.

As has been described above, the absorbance of the conventional reagent changes with two during storage before measurement. Thus, the POD activity cannot be measured with high accuracy.

SUMMARY OF THE INVENTION

Accordingly, the object of this invention is to provide a method which can measure POD activity with high accuracy using a reagent prepared in advance.

This object is achieved by a method of measuring peroxidase activity based on reaction of o-phenylendiamine and hydrogen peroxide in the presence of peroxidase, said method comprising the steps of:

preparing and storing a first reagent containing o-phenylendiamine and having a first pH value higher than a second pH value at which said reaction is conducted;

preparing and storing a second reagent having a buffering capability or capacity larger than said first reagent;

mixing said stored first and second reagents together with a sample containing peroxidase and a predetermined amount of hydrogen peroxide to provide a reaction mixture having said second pH value;

conducting said reaction in said reaction mixture, thereby producing 2,2'-diamino-azobenzene; and measuring absorbance increase at the maximum absorption wavelength of said 2,2'-diamino-azobenzene.

BRIEF DESCRIPTION OF THE DRAWINGS

FIG. 1 is a graph to illustrate the effect of one example of this invention; and FIG. 2 is a graph to illustrate the problems encountered in the conventional technique.

DETAILED DESCRIPTION OF THE PREFERRED EMBODIMENTS

In this invention, the hydrogen peroxide which is the substrate of the enzyme reaction by POD together with o-phenylenediamine, can be added in advance with the first reagent and/or the second reagent. Also, as a solution of hydrogen peroxide, this can be added as a third reagent. The predetermined amount of $H_2O_2$ is sufficient to produce detectable 2,2'-diamino-azobenzene by the absorbance measurement. It is preferable to use $H_2O_2$ in an amount greater than equivalent to OPD.

The OPD non-enzyme color reaction takes place readily under acidic condition, especially at pH=3.5~6.0, and takes place with difficulty in the pH range from neutral to the alkaline condition. So, the pH value of the first reagent used in this invention is adjusted to greater than 6.0, preferably greater than 7.0. In this pH range, non-enzyme color reaction of OPD does not easily occur, so the OPD in the reagent can remain for a long time. Therefore, its absorbance increase with time is extremely small.

It is desirable to store the first and second reagents in a cold and dark place, e.g., in a refrigerator.

Also, by mixing at least these two reagents at the time of measurement, the mixed reagent is used containing OPD needed for the foregoing enzyme reaction substrate and $H_2O_2$, and prepared to the optimum pH level of the foregoing reaction as well. Consequently, the formation of 2,2'-diamino-azobenzene is performed rapidly, and absorbance increase needed for the measurement of POD Activity is manifested very effectively, therefore the measurement of POD Activity is possible at high accuracy. The reaction is conducted at a temperature which does not deactivate POD. Room temperature is acceptable.

EXAMPLE 1

<Preparation of Reagent>

In the example, a first reagent was prepared by dissolving 90 mg of OPD and 300 μl of 2.33% solution of $H_2O_2$ into a 20 ml purified water. The pH value of this first example reagent was near 7.0. This was then poured in a brown bottle and stored in a dark place at 4° C.

Also, a buffer solution of pH=4.7 having the following composition was prepared as the second reagent. Other buffer solutions can also be used.

$Na_2HPO_4$; 0.3 mol/l
Citric Acid; 0.15 mol/l

The control (additional first reagents) were prepared by adding appropriate buffer solution to the foregoing first example reagent and adjusted to pH 4.7, 5.0 and 5.5, respectively.

<Stability Test of first Reagent>

The absorbance changes during storage of the first reagents were tested. The results are shown in FIG. 2. In this figure, curve "a" shows the result of the example reagent, and curves "b" to "d" shows the results of the control reagents. As is apparent from the figure, the absorbance change of the example reagent during storage is far smaller than the control reagents. This is attributable to the pH value of the example reagent, which makes it difficult for the OPD and $H_2O_2$ color reaction to take place. In other words, it is adjusted to pH=7.0 which is more alkaline condition rather than the optimum pH range of the reaction.

<Measurement of POD Activity>

POD activity of the sample was measured using the above-mentioned first and second example reagents.

First, 400 μl of the first reagent, and 100 μl of the second reagent were mixed. Since the first reagent practically has no buffering capability, the pH of the mixed solution was controlled by the pH value (pH=4.7) of the second reagent. This pH value is in the optimum level for the enzyme reaction by the POD. Now, this mixed reagent was added to five POD sample solutions (100 ml), which are products of Chemical Credential Company having the following concentrations, executed the enzyme reaction for OPD coloring and measured absorbance. Moreover, all of the following POD sample solutions contain 0.1% of BSA (Bovine Serum Albumin) to prevent the non-specific absorption of POD. Also, all the sample solutions are adjusted to pH=7.2 using 0.01 mol/l of PBS (Phosphate Buffered Saline).

Sample Solution 1: 0 mU/ml
Sample Solution 2: 0.784 mU/ml
Sample Solution 3: 1.568 mU/ml
Sample Solution 4: 3.136 mU/ml
Sample Solution 5: 6.273 mU/ml Each sample was measured five times, using the first reagent stored for 0 min, 30 min, 60 min, 90 min, 120 min, and 150 min, and the standard deviations (SD) of these measured values were calculated. In the absorbance measurement, POD was deactivated by adding 2 ml of 1 normal HCl, and after terminating the reaction, the absorbance was measured at 492 nm wavelength. This result is shown in Table 1. Absorbance A is expressed as $A = \log I_o/I$ when $I_o$ is the incident light intensity, and $I$ is the transmitted light intensity.

Furthermore, the maximum absorbance wavelength (λ max.) of the 2,2'-diamino-azobenzene at free condition is about 440 nm, but shifts to 492 nm at the protonated condition by adding the acid. Consequently, in the case of measuring without terminating the reaction, the measurement is made at 400 nm, but in the case of terminating the reaction by adding acid the measurement is taken at 492 nm.

TABLE 1

| | (Example) | | | | |
|---|---|---|---|---|---|
| | Absorbance | | | | |
| | Sample 1 | Sample 2 | Sample 3 POD | Sample 4 | Sample 5 |
| Time | 0 mU/ml | 0.784 mU/ml | 1.568 mU/ml | 3.136 mU/ml | 6.273 mU/ml |
| T0 | 0.0189 | 0.1899 | 0.4087 | 0.7677 | 1.7023 |
| T1 | 0.0246 | 0.1912 | 0.4146 | 0.7740 | 1.7092 |
| T2 | 0.0302 | 0.2031 | 0.4218 | 0.7773 | 1.7141 |
| T3 | 0.0362 | 0.2068 | 0.4259 | 0.7842 | 1.7230 |
| T4 | 0.0418 | 0.2119 | 0.4321 | 0.7896 | 1.7247 |
| T5 | 0.0497 | 0.2198 | 0.4395 | 0.7993 | 1.7311 |
| SD Value | 0.01267 | 0.01306 | 0.01261 | 0.01277 | 0.01203 |

Also absorbance measurements were performed to measure the POD activity by the conventional method on the above POD sample solutions for comparison. For these control measurements, only the first control reagent adjusted to pH=5.5 was used. The concrete measurement method is the same as the aforementioned embodiment. The results are shown in Table 2.

TABLE 2

| | (Control) | | | | |
|---|---|---|---|---|---|
| | Absorbance | | | | |
| | Sample 1 | Sample 2 | Sample 3 POD | Sample 4 | Sample 5 |
| Time | 0 mU/ml | 0.784 mU/ml | 1.568 mU/ml | 3.136 mU/ml | 6.273 mU/ml |
| T0 0 min | 0.0612 | 0.3382 | 0.5780 | 1.0703 | 2.0257 |
| T1 30 min. | 0.0851 | 0.3611 | 0.6002 | 1.0912 | 2.0500 |
| T2 60 min. | 0.1100 | 0.3829 | 0.6380 | 1.1121 | 2.0772 |
| T3 90 min. | 0.1298 | 0.4216 | 0.6535 | 1.1512 | 2.1033 |
| T4 120 min. | 0.1771 | 0.4301 | 0.6799 | 1.1712 | 2.1261 |
| T5 150 min. | 0.1896 | 0.4723 | 0.7001 | 1.1993 | 2.1480 |
| SD Value | 0.05656 | 0.05526 | 0.05197 | 0.05545 | 0.05179 |

As is evident from Tables 1 and 2 regarding each sample, the SD values of the absorbance measurement by this invention are smaller than the conventional method. This is because in the above embodiment, the non-enzyme color reaction of OPD has been eliminated, so it shows the excellent linear correlation between the passage of time and absorbance increase. Accordingly, the absorbance increase can be expressed more directly to the POD Activity, and improve the measurement accuracy.

Furthermore, the small SD values means that a steady measurement can be conducted at any time.

EXAMPLE 2

In this embodiment, a solution containing OPD 90 mg and 2.33% solution of $H_2O_2$ 300 μl was adjusted nearly to pH=12, by adding 20 ml of 0.1 mol/l NaOH solution. This solution was used as the first reagent.

As the second reagent for the pH control, a buffer solution of pH=4.7 with the same composition as Example 1 was used.

In this example, the first reagent containing OPD has been adjusted to have more alkaline pH than Example 1.

Therefore, the first reagent can be stored more stable than Example 1. As a result, the absorbance change of the first reagent was made to be smaller than Example 1. Thus a more higher accuracy measurement was possible.

EXAMPLE 3

In this example, use was made of a first reagent adjusted to pH=10.18 by dissolving a solution containing OPD 90 mg and 2.33% solution of $H_2O_2$ 300 μl in a 20 ml aqueous solution with a pH=10.18 containing 0.1 mol/l of disodium hydrogenphosphate $Na_2HPO_4$.

On the other hand, a pH=1.5, 0.1 mol/l phosphoric acid aqueous solution was used as a second reagent.

Also in this example, at the time of measurement, the first reagent having a high pH value was mixed with the second reagent having a low pH value, and adjusted to pH=4.7. This pH-adjusted reagent is added to POD sample, and measurement was performed after the color reaction had taken place.

According to this example, since the first reagent has its pH value adjusted by a weak base ($Na_2HPO_4$), its pH value is more stable than those of Examples 1 and 2 prepared with water or alkali solution.

Therefore, measurement with more stability and higher accuracy becomes possible.

As previously mentioned, because of this invention first reagent can be stored with long term stability and able to measure the POD activity with high accuracy at all times.

What is claimed is:

1. A measurement method of peroxidase activity based on reaction of o-phenylenediamine and hydrogen peroxide in the presence of peroxidase, said method comprising the steps of:
    preparing and storing a first reagent containing o-phenylenediamine and having a first pH value higher than 6, which first pH is higher than a second pH value at which said reaction is conducted;
    preparing and storing a second reagent having a buffering capacity larger than said first reagent;
    mixing said stored first and second reagents together with a sample containing peroxidase and a predetermined amount of hydrogen peroxide to provide a reaction mixture having said second pH value;
    conducting said reaction in said reaction mixture, thereby producing 2,2'-diamino-azobenzene; and
    measuring absorbance increase at the maximum absorption wavelength of said 2,2'-diamino-azobenzene.

2. The measurement method of peroxidase activity according to claim 1, wherein said first reagent further contains said predetermined amount of hydrogen peroxide.

3. The measurement method of peroxidase activity according to claim 1, wherein said second reagent further contains said predetermined amount of hydrogen peroxide.

4. The measurement method of peroxidase activity according to claim 1, wherein said first and second reagents both contain hydrogen peroxide, and provide said predetermined amount of hydrogen peroxide when mixed together.

5. The measurement method of peroxidase activity according to claim 1, wherein said predetermined hydrogen peroxide is supplied from source containing a solution of hydrogen peroxide.

6. The measurement method of peroxidase activity according to claim 1, wherein the pH value of said first reagent is adjusted from neutral to the alkaline condition.

7. The measurement method of peroxidase activity according to claim 1, wherein said second reagent is a buffer solution of pH=4.7.

8. The measurement method of peroxidase activity according to claim 1, wherein said absorbance increase is measured at a wavelength of 440 nm.

9. The measurement method of peroxidase activity according to claim 1, wherein said absorbance increase is measured at wavelength of 492 nm after said reaction is terminated by adding a strong acid to said reaction mixture.

10. The measurement method of peroxidase activity according to claim 1 wherein the first pH value is greater than 7.

11. The measurement method of peroxidase activity according to claim 10 wherein the pH of the second reagent is 4.7.

12. The measurement method of peroxidase activity according to claim 11 wherein said absorbance increase is measured at a wavelength of 440 nm.

13. The measurement method of peroxidase activity according to claim 11 wherein strong acid is added to said reaction to terminate it and thereafter said absorbance increase is measured at a wavelength of 440 nm.

14. The measurement method of peroxidase activity according to claim 2 wherein said absorbance increase is measured at a wavelength of 440 nm.

15. The measurement method of peroxidase activity according to claim 2 wherein strong acid is added to said reaction to terminate it and thereafter said absorbance increase is measured at a wavelength of 440 nm.

* * * * *